United States Patent [19]
Lai

[11] Patent Number: 4,601,839
[45] Date of Patent: * Jul. 22, 1986

[54] STABILIZED POLYMERS, NOVEL STABILIZERS, AND SYNTHESIS THEREOF

[75] Inventor: John T. Lai, Broadview Heights, Ohio

[73] Assignee: The B. F. Goodrich Company, Akron, Ohio

[ * ] Notice: The portion of the term of this patent subsequent to Jan. 12, 1999 has been disclaimed.

[21] Appl. No.: 320,991

[22] Filed: Nov. 13, 1981

Related U.S. Application Data

[63] Continuation-in-part of Ser. No. 916,639, Jun. 19, 1978, Pat. No. 4,310,429.

[51] Int. Cl.$^4$ .................. C10M 1/32; C10M 1/24
[52] U.S. Cl. .................. 252/51.5 A; 564/164; 564/193; 564/196; 564/201; 546/184; 546/192; 544/358; 544/359; 544/106; 548/255; 548/262; 524/81; 524/86; 524/186; 523/1; 523/500; 523/503; 523/508
[58] Field of Search ............... 564/164, 193, 196, 201; 252/51.5 A; 546/184, 192; 548/255, 262; 544/358, 359, 106; 523/503, 1, 508, 500; 524/81, 86, 186

[56] References Cited

U.S. PATENT DOCUMENTS

| 2,139,190 | 12/1938 | Iselin et al. ..................... 260/561 A |
| 2,153,707 | 4/1939 | Bechenen et al. ........... 260/561 A X |
| 2,499,352 | 3/1950 | Bruce et al. ..................... 260/588 A |
| 2,548,863 | 4/1951 | Bruce et al. ........................ 564/197 |
| 3,247,200 | 4/1966 | Ugi et al. ..................... 260/558 A X |
| 3,361,812 | 1/1968 | Hofer et al. ...................... 564/193 X |
| 3,428,646 | 2/1969 | Hellerbach ................. 260/558 A X |
| 3,446,806 | 5/1969 | Archer et al. ................... 564/164 X |
| 3,625,972 | 12/1971 | Schulenberg ............. 260/558 A X |
| 3,674,787 | 7/1972 | Frey et al. ................... 260/568 A X |
| 3,676,492 | 7/1972 | Biel et al. ........................ 564/164 X |
| 3,919,313 | 11/1975 | Villani ............................ 564/193 X |
| 3,944,607 | 3/1976 | Chan ............................ 260/558 A |
| 4,022,698 | 2/1978 | Hylton et al. ................... 564/164 X |
| 4,064,270 | 12/1977 | Wollweber et al. ....... 260/558 A X |
| 4,205,168 | 5/1980 | Chan ........................... 260/558 A X |
| 4,310,429 | 1/1982 | Lai ................................. 252/51.5 A |

Primary Examiner—Paul F. Shaver

[57] ABSTRACT

Novel α-aminoacetamides are powerful stabilizers for organic materials subject to oxygen and heat degradation, and particularly for synthetic natural rubber, synthetic ester lubricants and synthetic resinous materials. A wide range of substituents on the amine and amide N atoms, at least one of which substituents is an alkylene imine (cyclic), and an even wider range of substituents on the saturated carbon atom, yields an array of stabilizers having a wide range of compatibility in compositions comprising various synthetic resinous compounds to be stabilized.

Novel syntheses are provided utilizing at least one amine nucleophilic agent, a trichloromethide ion generating agent, and an alkoxide ion generating agent, which together in the presence of aqueous alkali and an onium salt, yield novel α-aminoacetamides in which a wide choice of substituents may be introduced. The nucleophilic agent may be a primary or secondary amine, or one of each. The trichloromethide ion generating agent is a haloform. The alkoxide ion generating agent may be a ketone, or an aldehyde which reacts with the haloform.

16 Claims, No Drawings

STABILIZED POLYMERS, NOVEL STABILIZERS, AND SYNTHESIS THEREOF

CROSS-REFERENCE TO RELATED APPLICATION

This is a continuation-in-part application to Ser. No. 916,639 filed June 19, 1978, now U.S. Pat. No. 4,310,429.

BACKGROUND OF THE INVENTION

Any material, whether natural or synthetic must exhibit satisfactory resistance to degradation under conditions of use, if products made from the materials are to find a lasting market. A lack of satisfactory resistance to degradation usually manifests itself as a partial or total loss of structural integrity, a darkening or discoloration of the product, a loss of flexibility or resilience, or a combination of the above phenomena. These phenomena are promoted or catalyzed by air (oxygen), heat and light, and are particularly susceptible to autooxidation at elevated temperatures in the presence of oxygen.

To protect organic materials, ingredients which can be collectively called stabilizers are admixed with the materials to prevent or inhibit degradation. These stabilizers work in diverse and complex ways, such that a compound which stabilizes against oxygen degradation in one type of material may be relatively inactive in another type of material. Thus compounds which are stabilizers are further classed as anti-oxidants, antiozonants, heat stabilizers and ultraviolet (UV) light stabilizers, depending upon what type of activity and stabilization they best demonstrate. In many cases, to obtain optimum protection, a mixture of compounds, each specifically selected to afford maximum protection against a certain type of degradation, is often used. In some instances stabilizers are deliberately chosen to counter the adverse effects of a plasticizer which, though highly effective as a plasticizer, tends to accelerate oxygen and heat degradation. In other words, the plasticized material is more susceptible to degradation than if no plasticizer was added. As a general empirical rule, it is found that plasticizers are marginally effective as stabilizers, and stabilizers are marginally effective as plasticizers, it being more likely that a compound with desirable stabilizer properties has undesirable plasticizer properties, and vice versa.

The stabilization of rubber, and particularly synthetic "natural rubber", is essential for its proper functioning and long life. To protect rubber against deterioration, many new compounds have been synthesized and tested. Although most anti-oxidants give good protection as stabilizers, not all stabilizers give satisfactory anti-oxidant activity (Encyclopedia of Polymer Science and Technology, Vol. 12, btm p 267, Interscience Publishers, New York, 1970). The compounds of this invention are primarily antioxidants though they exhibit other desirable stabilizing properties, and are particularly for use in synthetic ester lubricants, generally known as "functional fluids", and in synthetic diene rubbers, as a primary antioxidant, i.e. as the sole antioxidant, or if desired, may be combined with a secondary antioxidant which serves to enhance the stabilizing performance of the primary antioxidant. When used with a secondary antioxidant, the stabilizing effect achieved is synergistic and the performance substantially exceeds the sum total of the performances exhibited by the individual antioxidant components.

The time-tested rubber antioxidants chemically classed as amines and phenols and their respective derivatives are still being used, but newer antioxidants combine a hindered phenol group with another group containing sulfides, triazine, phosphates, phosphites, etc. with the hope that the active materials will combine the advantages of two or more stabilizing moieties.

The compounds of this invention do not belong to any well-recognized chemical class of antioxidants. They are substituted acetamides, and more particularly substituted α-aminoacetamides. It is worth noting that known antioxidants formed by reactions of aldehyde-amines have only fair oxygen aging, and reaction products of ketone-amines generally have only good oxygen aging (Kirk & Othmer, Encyclopedia of Chemical Technology, 2d Edition, Vol 17, p 526, Interscience Publishers, New York, 1968).

As is well-known to those skilled in the art, the effectivness of an antioxidant organic is predicated upon the oxidizable material in which the antioxidant is used. Thus, though antioxidants are used in plastics, elastomers, petroleum products, synthetic lubricants, food products, paints, soaps and cosmetics, it is seldom that the same type of antioxidant will be useful in a plastic or elastomer, and a petroleum or synthetic lubricant. Yet the compounds of this invention provide just such a multifunctional purpose, being useful in several synthetic resinous materials including plastics, elastomers and particularly conjugated diene polymers and synthetic functional fluids of the type generally classed as di- and polycarboxylate type ester lubricants.

Various amides have been found useful as antioxidants. For example, water-soluble antioxidants such as amides of phenol substituted acids have been produced by reaction of reactive derivatives of corresponding acids with corresponding amino compounds to form acid amides, as disclosed in U.S. Pat. No. 3,665,031. Conventional methods of amide preparation also yield alkylhydroxybenzylamides as taught in U.S. Pat. No. 3,780,103. A reaction between selected alkylaminophenols and thiodialkanoyl acid chlorides yields thiodialkanoamidophenol compounds; related compounds are disclosed in U.S. Pat. Nos. 3,676,494; 3,679,744 and 3,694,375. None of the foregoing conventional methods of amide preparation yields the compounds of this invention.

It was known a long time ago, that the reaction of chloretone(1,1,1-trichloro-2-methyl-2-propanol) with aniline and KOH in ethanol, yields α-phenylaminoisobutyric acid anilide, also referred to as α-dimethyl, α-analino, analinoacetamide, though in poor yields. See G. Banti, Gazz. Chim. Ital. 59, 819–24 (1929). Furthermore, this reaction is applicable only to aniline and substituted anilines, and even so, compounds higher in molecular weight than chloretone and aniline, give progressively poorer yields.

The present invention is particularly directed to (a) novel antioxidants and heat stabilizers classed as hindered acetamides, more specifically classed as hindered alpha-aminoacetamides, (b) novel compositions in which the α-aminoacetamides are incorporated, and (c) novel syntheses for the α-aminoacetamides. The basic structure of these novel compounds is an α-aminoacetamide which is preferably polysubstituted. Though these novel compounds are acyclic, they may have cyclizable substituents, and may form dimers and bis-compounds.

The novel compounds of this invention are unrelated to amino acids and are not derived from them.

The synthesis of the novel stabilizers of this invention is made possible by the peculiar action of certain onium salts in an aqueous alkaline medium, which action facilitates the interaction of an amine nucleophilic agent such as a primary or secondary amine, with chloroform or other trichloromethide generating agent, and a ketone, aldehyde, cyanohydrin or other alkoxide ion generating agent. The organic onium salts of nitrogen, phosphorus and sulfur are well known. They are ionized in aqueous solutions to form stable cations. Certain onium salts have provided the basis for phase transfer catalysis in a wide variety of reactions, a recent and comprehensive review of which is contained in Angewandte Chemie, International Edition in English, 16 493-558 (August 1977). Discussed therein are various anion transfer reactions where the onium salt exchanges its original anion for other anions in the aqueous phase. These ion pairs can then enter a water immiscible, organic liquid phase, making it possible to carry out chemistry there with the transported anion, including OH⁻ ions. Many reactions involving water immiscible solutions of various simple organic molecules have been described. However, there is nothing to suggest the phase transfer catalysis of a reactants described in my invention.

The first disclosure relating to the phase transfer catalyzed ("PTC" for brevity) synthesis of compounds claimed in the parent application Ser. No. 916,639 of this continuation-in-part application was made in an oral presentation titled "Hindered Amines. Synthesis of Hindered Acyclic α-Aminoacetamides" published in the Journal of Organic Chemistry, 45, 3671-3 (1980). A more detailed discussion of the theoretical considerations relevant to the subject matter than is presented in this application, is presented therein. Also, it has now become evident that the formation of the dichlorocarbene ion postulated in my parent application is in error, and that, as I now understand the reaction, a trichloromethide ion is generated which subsequently combines with the ketone (or aldehyde) forming an oxirane intermediate. In my copending application Ser. No. 250,826 filed Apr. 3, 1981 I have disclosed another PTC synthesis of an alpha-substituted acetamide by the condensation of a primary or secondary amine with an alpha-haloacetamide.

SUMMARY OF THE INVENTION

Substituted α-aminoacetamides have been discovered which are excellent stabilizers for organic materials, and especially for ultraviolet light-sensitive synthetic resinous materials, conjugated diene polymers and lubricants known as "functional fluids" of the synthetic polycarboxylate type. Specific conjugated diene polymers are natural and synthetic rubbers such as are used in the manufacture of vehicle tires, belting, rubber hose and the like. Specific functional fluids of the polycarboxylate type are those having from 2 to about 8 carboxylate groups per molecule.

Novel compositions have been discovered comprising an organic material subject to the deleterious effects of oxygen heat and light, and from about 0.001 percent to about 10 percent by weight of a substituted alpha-aminoacetamide aminoacetamide having at least one alkylene imine substituent (cyclic) on the amine or amine N atoms, dispersed therein.

It has also been discovered that polysubstituted alpha-aminoacetamides, may be directly synthesized, catalytically, in the presence of onium salts using readily available starting materials, in conventional apparatus, under ambient temperature and pressure conditions. In these syntheses, an alkoxide ion generating agent selected from the group consisting of a ketone and an aldehyde is reacted with a trichloromethide ion generating agent, e.g. a haloform, under alkaline conditions with an amine nucleophilic agent such as a primary and/or secondary amine in the presence of an onium salt to yield an alpha-aminoacetamide. Substituents on the α-aminoacetamide may be introduced by an appropriate choice of substituents on the alkoxide ion generating agent, and, substituents on the amine nucleophilic agent.

DETAILED DESCRIPTION OF PREFERRED EMBODIMENTS

The substituted alpha-aminoacetamides of this invention, used to stabilize organic materials, are primarily anti-oxidant stabilizers (referred to as 'antioxidants'), ultraviolet light stabilizers and heat stabilizers, which exhibit excellent performance when dispersed in organic materials subject to oxidative, thermal and photochemical degradation. Most particularly these stabilizers are antioxidants for synthetic natural rubber and synthetic ester lubricants, and have a balance of properties which permits the stabilizers to be used primarily as antioxidants and heat stabilizers with complementary light-stabilization effects without significant loss of flexibility or abrasion of the stabilized material.

It is especially significant that these relatively low molecular weight compounds contain a substituted amino group attached to an acetamide group, each of which groups may be independently substituted with moieties having not only desirable antioxidant properties, but also heat stabilizing properties complemented with suitable solubility and dispersability.

The substituted acetamides are generally oils or high melting crystalline solids soluble in acetone, diethyl ether, dioxane, tetrahydrofuran, carbon tetrachloride, chloroform, aromatic hydrocarbons such as benzene and toluene, but much less soluble in aliphatic hydrocarbons and lower alcohols such as methanol and ethanol. Substituted acetamides are generally insoluble in water; they range in color from white to dark brown when pure. Certain substituted acetamides are more useful for particular applications than others, due to the compatibility of the acetamides with the organic material to be stabilized. This is the result of a variety of factors such as the type of substituents on the alpha C atom, the particular substituents on the amine N atom, and amide N atom, and the physical properties of the acetamide. The amount of antioxidant employed will vary with the particular material to be stabilized and also the substituted acetamide employed. Generally however, for effective stabilization of organic materials, an amount of the antioxidant used is in the range from about 0.001 percent to about 10 percent by weight (% by weight) based on the weight of organic material. In typical stabilized compositions the amount of substituted acetamide used is in the range from about 0.01 to about 5% by weight.

Compositions of this invention are synthetic resinous materials and synthetic lubricants which have been stabilized to combat the deleterious effects of thermal or oxidative degradation such as are usually evidenced by discoloration and/or embrittlement. These compositions generally benefit from the inclusion of additional, secondary UV stabilizers to achieve even greater stability against a combination of actinic light, heat and oxygen. Therefore, in conjunction with the stabilizers of this invention, compositions may include UV light stabilizers in the range from about 0.1 part to about 10 parts by weight, and preferably from about 0.2 part to about 5 parts by weight per 100 parts by weight of the organic continuous phase. Several types of known UV stabilizers may be used, such as those disclosed in U.S. Pat. Nos. 3,325,448; 3,769,259; 3,920,659; 3,962,255; 3,966,711; 3,971,757; inter alia.

The organic materials to be stabilized may be low or high molecular weight materials, and particularly include homopolymers, copolymers and mixtures thereof. Most preferred examples of organic materials present as the continuous phase, which can be stabilized against thermal and oxidative degradation by substituted acetamides are natural rubber; synthetic rubbers formed from conjugated dienes such as cis-polyisoprene, polybutadiene, styrene-butadiene rubber, diene-nitrile rubbers, polyepihalohydrin polymers, and the like; and, functional fluids of the polycarboxylate type formed by reacting a polycarboxylic acid with a mono-hydric alcohol, or alternatively, by reacting a monocarboxylic acid with a polyhydric alcohol.

Illustrative of the functional fluids which can be employed in the present invention are the following dicarboxylates such as oxalates, malonates, succinates, glutarates, adipates, pimelates, suberates, azelates, sebacates and the like; tricarboxylates such as the triesters of trimethylolpropane and tricarboxypentane, tetracarboxylates such as the tetraesters of pentaerythritol, and the higher polycarboxylates such as the esters of di- and tripentaerythritol. Mixtures of these esters can also be employed. When a polycarboxylic acid is used to make the polycarboxylate, the alcohol moiety of these esters normally has between 4 and 18 carbon atoms and preferably from 6 to 12 carbon atoms. Likewise, when a polyhydric alcohol is used to make the polycarboxylate, the carboxylic moiety normally has from 4 to 18 carbon atoms and preferably from 4 to 12 carbon atoms. Mixtures of the above described esters can also be used. The preferred base stocks are of the trimethylolpropane and pentaerythritol ester type. Particularly preferred is a mixture of trimethylolpropane triheptanoate and pentaerythritol monobutyrate triheptanoate. These esters can also be cross-linked by employing a cross-linking agent such as azelaic acid when synthesizing them as is well known in the art.

The base stocks into which the present antioxidants are incorporated can also contain minor amounts by weight of hydrocarbon lubricants and other well known functional fluid additives. Typical of these latter additives are the following, with the normal ranges in weight percent of the entire fluid being given in the parenthesis:

(a) Viscosity index improvers such as the polymers of acrylic and metha-crylic acid esters which are normally incorporated in a suitable carrier (0.5-5%);

(b) Lubricity and extreme pressure additives of the organo phosphorus type, particularly the organic phosphite, phosphonates, phosphates and amine salts thereof, as exemplified by the hydrogen phosphonates, triaryl phosphates and the amine salts of dialkyl phosphorus acid esters (0.1-5%);

(c) Metal deactivators such as benzotriazoles and the N,N'-disalicyli-dene-dialkyl diamines (0.001-1%); and (d) Antifoaming agents of the silicone variety, particularly the methyl silicones and siloxanes (0.0001 to 0.002%).

Other organic materials which may be stabilized against thermal and oxidative degradation include other copolymers of butadiene with acrylic acid, alkyl acrylates or methacrylates, polyisoprene, polychloroprene, and the like; polyurethanes; vinyl polymers known as PVC resins such as polyvinyl chloride, copolymers of vinyl chloride with vinylidene chloride, copolymers of vinyl halide with butadiene, styrene, vinyl esters, and the like; polyamides such as those derived from the reaction of hexamethylene diamine with adipic or sebacic acid; epoxy resins such as those obtained from the condensation of epichlorohydrin with bisphenols, and the like; ABS resins, polystyrene, polyacrylonitrile, polymethacrylates, poly-carbonates, varnish, phenol-formaldehyde resins, polyepoxides, polyesters, and polyolefin homo- and copolymers such as polyethylene, polypropylene, ethylene-propylene polymers, ethylene-propylenediene polymers, ethylene-vinyl acetate polymers, and the like. The substituted amino amides can also be used to stabilize mixtures and blends of polymeric materials such as ABS resin blends, PVC and polymethacrylate blends, and blends of polyolefin homopolymers and copolymers such as blends of polypropylene in epdm polymers. Most particularly substituted alpha-aminoacetamides of this invention having at least one cyclic alkylene imine substituent on one of the two N atoms of the acetamide, are especially useful as light-stabilizers for synthetic resinous materials and as antioxidants for synthetic natural rubber and synthetic ester high temperature lubricants.

Many known compounding ingredients may be used along with the substituted acetamide stabilizers in the compositions. Such ingredients include metal oxides such as zinc, calcium and magnesium oxide, fatty acids such as stearic and lauric acid, and salts thereof such as cadmium, zinc and sodium stearate and lead oleate; fillers such as calcium and magnesium carbonate, calcium and barium sulfates, aluminum silicates, asbestos, and the like; plasticizers and extenders such as dialkyl and diaryl organic acids like diisobutyl, diisooctyl, diisodecyl, and dibenzyl oleates, stearates, sebacates, azelates, phthalates, and the like; ASTM type 2 petroleum oils, paraffinic oils, castor oil, tall oil, glycerin, and the like.

The substituted acetamide stabilizers, and the other compounding ingredients if used, can be admixed with organic materials using known mixing techniques and equipment such as internal mixing kettles, a Banbury mixer, a Henschel mixer, a two-roll mill, an extruder mixer, or other standard equipment, to yield a composition which may be extruded, pressed, blowmolded or the like into film, fiber or shaped articles. Standard mixing times and temperatures can be employed. The objective is to obtain intimate and uniform mixing of the components. A favorable mixing procedure to use when adding a substituted acetamide to an organic material is either to dissolve or suspend the compound in a liquid such as hexane or benzene, add it to the organic material in the form of a powder to the solution or suspension, and extruder-mix the stabilized organic material prior to forming the product.

Samples of the compositions can be checked for oxidative and thermal stability by measuring the time to discoloration and/or embrittlement of the sample after aging in an air circulating oven at 140° C. and other standard ASTM tests.

The novel substituted acetamides of this invention may be represented by the general structural formula:

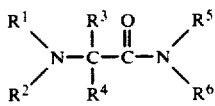

wherein at least one of R¹, R², R⁵ and R⁶ substituents is alkylene imine having from 5 to 8 carbon atoms in which hydrogen atoms may be substituted with alkyl groups having from 1 to about 24 carbon atoms, and, when one substituent on either N atom is alkylene imine, the other substituent on that N atom represents hydrogen or said alkyl; and R³ and R⁴ independently represent the following substituents: hydrogen; aryl, alkyl having from 1 to 24 carbon atoms wherein functional groups may be substituted with alkyl groups; hydroxyalkyl having from 1 to about 12 carbon atoms; haloalkyl having from 1 to about 12 carbon atoms; cyanoalkyl having from 2 to about 12 carbon atoms; aminoalkyl or iminoalkyl having from 1 to about 12 carbon atoms; ether groups having from 3 to about 18 carbon atoms; hydroxyalkyl ether or cyanoalkyl ether groups having from 4 to about 18 carbon atoms; alkenyl and aralkyl having from 7 to about 14 carbon atoms; alkylene having from 1 to about 7 carbon atoms; alkenylene having from 2 to about 10 carbon atoms; each substituent optionally containing a phosphite, ester or hindered phenol group, and each substituent in combination, R³ with R⁴, may form a ring containing from about 5 to about 9 ring atoms, which ring may also contain hetero atoms such as N, S or O, and optionally contain a keto, ester, amide, ether or thio group.

By "alkylene" is meant a bivalent group derived by the removal of one H atom from two different carbon atoms of an alkane, but also includes methylene which, as an exception, is obtained by the removal of two H atoms from the same carbon atom. Examples of short chained alkylene subtituents are methylene (—CH₂—), ethylene (—CH₂—CH₂—), 1,2-propylene (—CH₃—CH—CH₂—), 1,3-propylene (—CH₂—CH₂—CH₂—), butylenes and the like. The term "alkenylene" is defined in an analogous manner as "alkylene", except that the H atoms are removed from an alkene. Examples of alkenylene substituents are vinylene (—C=CH—), propenylene (—CH₂—CH=CH—), butenylene, pentenylene, hexenylene, and the like.

Preferred stabilizers of this invention are those in which an alkylene imine substituent is present on at least one of the amine or amide N atoms. If an N atom has the alkylene imine substituent, then the other substituent on that atom is either hydrogen or alkyl having from 1 to about 24 carbon atoms. If each N atom has an alkylene imine substituent, then the other substituent on each N atom is either hydrogen or said alkyl. The substituents on an N atom which has no alkylene imine substituent may each be acyclic, or each be cyclic, or one may be acyclic and one cyclic, or the substituents may form a ring having only carbon atoms, except of course for the N atom in that ring. Preferred rings contain 5 or 6 ring atoms, and may be substituted, hence are referred to as optionally subsituted rings. Examples of such optionally substituted rings having only one heteroatom, that is N, are those which are derived from pyrrole, pyrrolidine and piperidine. Examples of optionally substituted rings containing more than one heteroatom are those derived from triazole, oxazolidine, piperazine, morpholine and diazepine.

The substituted acetamides of this invention may be grouped as those having:

(A) only one substituent on the alpha C atom;

(B) two substituents on the alpha C atom, each of which may be acyclic;

(C) two substituents on the alpha C atom, one of which is cyclic and the other acyclic; and (D) cyclized substituents on the alpha C atom.

The foregoing grouping according to substituents on the alpha carbon atom is the same as the grouping of compounds of my parent application, but in addition, the substituted acetamides of this invention may be further grouped as those containing one or more of the following:

(E) an alkylene imine substituent on the amine N atom, the other substituent on this N atom being either hydrogen or alkyl;

(F) an alkylene imine substituent on both the amine and the amide N atoms, the other substituent on each of the N atoms being either hydrogen or alkyl; and (G) substituted as in (E), and the substituents on the amide N atom may each be acyclic, each be cyclic, one be acyclic and one cyclic, or together they may form a ring (be cyclized).

Specific illustrative examples of compounds of this invention are those which may belong to any one of the groups (A) through (D), and which in addition belong to groups (E) through (G). Whatever the substituents on the alpha carbon atoms, the preferred compounds of this invention have an alkylene imine substituent and one acyclic substituent on either the amine N atom, or both the amine and amide N atoms, most preferred being the latter, namely those with one alkylene imine substituent and one acyclic substituent on both the amine and amide N atoms.

Particular compounds illustrative of the alkylene imine-substituted acetamides of this invention are listed hereinbelow along with their structural formulae, except that the methyl (alkyl) substituents on the alkylene imine are indicated by lines only.

Some compounds of the foregoing groups may be synthesized in the absence of an onium salt catlayst though it will be apparent that in most such catalyst-free processes the reaction proceeds so slowly as not to be as desirable as one in which an onium salt catlayst is used.

Groups D and E:

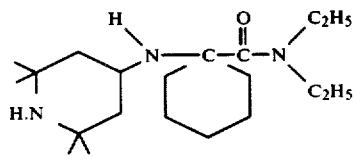

2-(4-2,2,6,6-tetramethylpiperidine)-
amino-2-pentamethylene-diethyacetamide

Groups B and F:

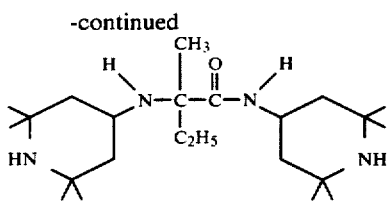

2-(4-2,2,6,6-tetramethylpiperidine)-amino-2-methyl-
N—(4-2,2,6,6-tetramethylpiperidine)-butanamide Groups B and G:

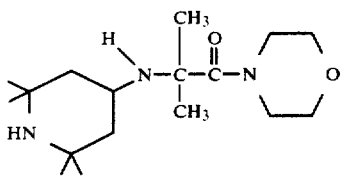

2-dimethyl,2-(4-2,2,6,6-tetramethylpiperidine)-
amino-acetamorpholinide

From the foregoing illustrative examples it will now be evident that various combinations of the above identified groups may be produced in a wide range of compounds. Those skilled in the art will appreciate that some compounds are more easily prepared than others, being affected by such considerations as steric hindrance, basicity of reactants, formation of byproducts, and the like. Of essential significance is the fact that, with a little routine trial and error, a substituent deemed likely to have a beneficial effect in a particular substituted acetamide to be used in a particular organic material, may be introduced directly due to the catalytic action of an onium salt in an alkaline aqueous medium. In particular, dimers and bis compounds of the substituted acetamides may also be prepared by known methods once the desired acetamide is obtained by a chosen onium salt catalyzed synthesis. A dimer may be linked through any one of the substituents $R^1$-$R^6$. The compounds of this invention may be further modified with additional steps well known to those skilled in the art.

In each preferred embodiment, the substituted acetamides are conveniently prepared from an amine nucleophilic agent and an alkoxide ion generating agent at ambient conditions in the critical presence of an onium salt under aqueous alkaline conditions. By aqueous alkaline conditions I refer to an aqueous solution of an alkali metal hydroxide containing from about 5% to about 75% by wt, and preferably from about 30% to about 50% by wt of alkali metal hydroxide. Preferred alkali metal hydroxides are those of sodium and potassium. By an amine nucleophilic agent I refer to an amine which is capable of attacking the epoxide ring, which it is hypothesized is formed as an intermediate under the alkaline conditions of this reaction. Primary and secondary amines are such agents.

It is critical for the overall reaction to occur, that an onium salt be present in an aqueous alkaline medium. Onium salts of sulfur, or of any element of Group VA of the Periodic Table, having certain structural limitations, may be used in which a preferred salt has the formula $R_nY^+X^-$, where Y is chosen from N P and S; R represents either different or identical monovalent organic radicals bonded to Y by covalent linkages; $X^-$ is a counterion; and n is an integer which may be 3 or 4. When Y is pentavalent, for example P or N, then n=4, and when Y is tetravalent, for example S, then n=3. In an analogous manner, onium salts having certain multivalent organic substituents may be useful in this invention. Examples include multivalent organic radicals that include Y in a ring, and those that are bonded to more than one Y.

More preferred onium salts for use in this invention have the formula $(R_aR_bR_cR_dY^+)X^-$ wherein Y is N or P, and $R_a$-$R_d$ are monovalent hydrocarbon radicals preferably selected from the group consisting of alkyl, alkenyl, aryl, alkaryl, aralkyl, and cycloalkyl moieties or radicals, optionally substituted with suitable heteroatom-containing functional groups. The total number of carbon atoms in $R_a$, $R_b$, $R_c$, and $R_d$ if the salt is quaternary, should be at least 10 and is preferably in the range from about 15 to 40. No theoretical maximum number of carbon atoms for inclusion in the onium salts exists, although in general, about 70 carbon atoms represents the upper limit imposed by practical limitations. Since the liquid phases involved are aqueous and organic, the number of the carbon atoms and structure of the onium salts are usually selected to impart to the salt a marked solubility in the organic phase. The onium salt itself is nonreactive with respect to all materials in the reaction mixture except the reactants themselves.

Most preferred onium salts have Y=N, and hydrocarbon radicals where $R_a$ is $C_2H_5$, and $R_b$, $R_c$, and $R_d$ are each selected from the group consisting of n-$C_4H_5$; n-$C_5H_{11}$; mixed $C_5H_{11}$; n-$C_6H_{13}$; mixed $C_6H_{13}$; $C_6H_5$; $C_6H_5CH_2$; n-$C_8H_{17}$; n-$C_{12}H_{25}$; n-$C_{18}H_{37}$; mixed $C_8$-$C_{10}$ alkyl; and the like. However, $R^1$ may also be selected from $C_2H_5$, n-$C_3H_7$ and n-$C_4H_9$.

Various counterions may be used, including $Cl^-$, $Br^-$, $I^-$, $F^-$, $SO_4$, $HSO_4^-$ and the like. Most preferred is $Cl^-$.

In addition to the above-described specific structure of the onium salt, the amount of the salt used is in the range from about 0.01 mol to about 10 mols, and more preferably, for the usual practice of this invention, from about 1 to about 3 mpha (mols per 100 mols of amine nucleophilic agent) used. The amount of salt used is not critical, the optimum amount in each case being easily determined by simple trial and error. An amount greater than about 10 mpha is uneconomical and serves no useful purpose.

In one preferred embodiment, an amine nucleophilic agent, whether a primary or a secondary amine, or one of each, is reacted with a ketone or aldehyde, and a haloform to yield a substituted acetamide. The precise mechanism of the reaction is not fully understood, but a mechanism is hypothesized.

The overall reaction which occurs with different secondary amines, a ketone and chloroform requires equimolar amounts of chloroform and amine nucleophilic agent, and may be represented as follows:

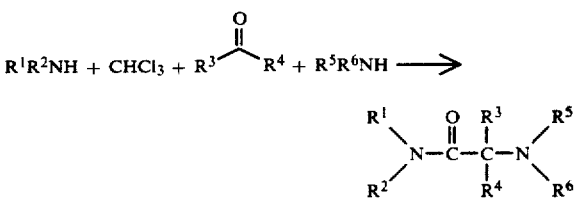

where the reaction occurs in an aqueous alkaline solution of an onium salt present in an amount in the range from about 0.01 to about 10 mole percent based on 100 moles of nucleophilic agent.

The foregoing reaction may be represented as occurring in a series of steps which may be set forth as follows:

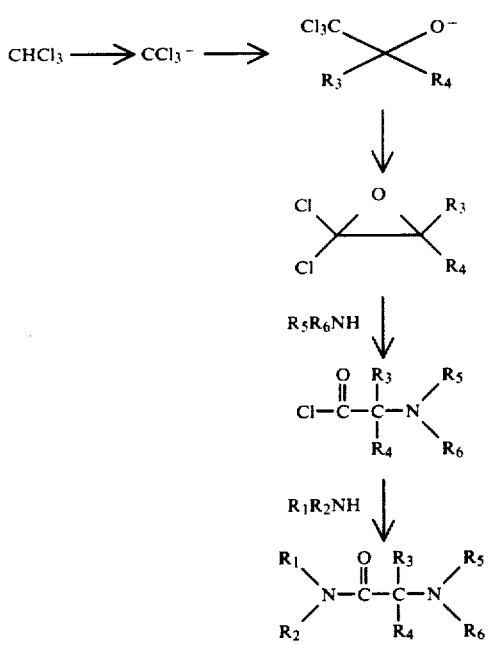

Typically the reactants are mixed into the organic phase, the order being unimportant. The aqueous alkali is then added to the system, with stirring, and heat is removed by cooling since the reaction is generally exothermic. The reaction proceeds at atmospheric pressure, and pressure considerations are not critical to the practice of the invention except as the requirements of a particular system may dictate.

Preferred organic solvents are essentially inert under the conditions of the reaction, and are immiscible in water. Most preferred are common aromatic and paraffinic solvents such as benzene, p-xylene, toluene, dichloromethane, chlorobenzene, cyclohexane and the like.

The invention is illustrated with the following examples:

EXAMPLE 1

2-(4-2,2,6,6-tetramethylpiperidine)-amino-2-pentamethylene-diethylacetamide, a compound of Groups D and E and having the structure identified hereinabove, is prepared as follows:

To introduce the alkyleneimine substituent the compound 4-amino-2,2,6,6-tetramethylpiperidine, an alkyleneimine with an amine substituent, also referred to herein as 'alkyleneimine amine', is first synthesized by known methods. This reactant may be either a primary or a secondary amine. The primary amine has the following structure:

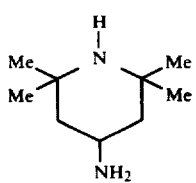

-continued

Me = methyl

Into a 500 ml three-necked flask fitted with a reflux condenser about 12.5 g of 4-amino-2,2,6,6-tetramethylpiperidine, 22 g diethylamine and 100 ml dichloromethane, followed by 9.8 g cyclohexanone and 13 g chloroform. Then 0.57 g benzyltriethylammonium chloride (hereafter "BTEA" for brevity) is added, followed by the dropwise addition of 40 ml 50% NaOH. The addition took about 15 min. The reaction was initiated at about 0° C. to 5° C., and being exothermic, the temperature is controlled in this temperature range. The reaction mixture is held at about 10° C. overnight while stirring, after which it was worked up. Typically, a reaction mixture is worked up by extracting with dichloromethane, washing several times with water, drying and concentrating. The structure of the compound was confirmed by gas chromatographic (GC), infrared (IR), and nuclear magnetic resonance (NMR) analysis.

Whenever, as above, it is desired to provide an alkyleneimine susbtituent on the amine N atom, and substituents other than an alkyleneimine on the amide N atom, it is generally preferable to provide, in addition to the alkyleneimine amine reactant, a secondary amine which is relatively less nucleophilic than it. This facilitates the substitution on the amide N atom. Such relatively less nucleophilic secondary amines are alkyl amines having a total of more than 3 carbon atoms. If only an alkyleneimine amine is used as the reactant, then the alkyleneimine substituent will appear at both the amine and amide N atoms, as will be illustrated in the next example.

EXAMPLE 2

In a manner analogous to that described in Example 1 hereinabove, 2-(4-2,2,6,6-tetramethylpiperidine)-amino-2-methyl-N-(4-2,2,6,6-tetramethylpiperidine)-butanamide, a compound of Groups B and F having the structure identified hereinabove is prepared as follows:

Into a 500 ml three-necked flask fitted with a relux condenser is placed 6.25 g of 4-amino-2,2,6,6-tetramethylpiperidine dissolved in 10 ml of dichloromethane, along with 1.74 g acetone and 3.58 g chloroform. Then 0.57 g "BTEA" is added, followed by the dropwise addition of 8 g of 50% NaOH. The addition took 2 min. The reaction was initiated at below 18° C., but being exothermic, an ice bath was used to keep the temperature at about 15° C. Thereafter the reaction mixture was allowed to rise to about room temperature at which it was stirred under argon overnight. A GC analysis showed the reaction was substantially complete in about 1 hr after the addition of all the reactants. The reaction mass was worked up with 100 ml of dichloromethane and 10 ml water, dried and concentrated. 7.6 g of pure white crystals were obtained. Recrystallization from hexanes produced 4.2 g of a white solid. The mother liquor was concentrated and yielded another 1.6 g of pure white powder, for a total yield of about 76%.

The structure of the compound was confirmed by gas chromatographic (GC), infrared (IR), and nuclear magnetic resonance (NMR) analysis.

EXAMPLE 3

In a manner analogous to that described in Example 2 hereinabove, 2-dimethyl,2-(4-2,2,6,6-tetramethylpiperidine-amino-acetamorpholinide, a compound of Groups B and G having the structure identified hereinabove is prepared by reacting 4-amino-2,2,6,6-tetramethylpiperidine dissolved in 10 ml of dichloromethane, morpholine and chloroform.

The structure of the compound was confirmed by gas chromatographic (GC), infrared (IR), and nuclear magnetic resonance (NMR) analysis.

The efficacy of alkyleneimine-substituted acetamides as antioxidants to retard oxidative degradation of synthetic natural rubber (SNR) is measured by ASTM-D-1646-72 testing procedure. The SNR used was obtained by solution polymerization of isoprene which yielded about 99% 1-4 cis addition product and 0.8% trans 1-4 addition product. The level of antioxidant used is 1 part per 100 parts SNR in all tests, using a large rotor and 1 min warm-up time. Mooney buttons were aged at 70° C. for 10 days in an oven in accordance with testing procedure ASTM-D-573-67.

The control was Stalite*S p,p'-dioctyl-diphenylamine, an antioxidant commercially available from the B. F. Goodrich Company, Akron, Ohio. The percent change in Mooney viscosity is the measure of antioxidant effectiveness; the lower the percent change, the more effective is the antioxidant. In general, the % change obtained with the compounds of this invention were about the same as, or lower than those obtained with Stalite S.

The efficacy of alkyleneimine-substituted acetamides as antioxidants and stabilizers against heat degradation of a functional fluid such as a synthetic ester lubricant is evaluated according to a modified Federal Test Method Standard Number 791a, Method 5308.5 (July 27, 1964). This is an oxidation test at 215.5° C. (420° F.) of a functional fluid containing a stabilizer which is simply blended into the fluid. The test is performed in the presence of air and 5 different metals such as copper, silver, magnesium, aluminum and steel. The test fluid chosen is di(2-ethylhexyl)sebacate (available from Hercules Chemical Company, Wilmington, Del. under the trade mark Herculube A). The fluid is poured into a large test tube equipped with an air bubbler, a holder for the metals and a condenser. The test tube is placed in a heated block and the temperature raised to 215.5° C. Air is then bubbled through the fluid at a rate of about 5 liters per hour over a 72 hour interval.

At the end of each test, the sample is evaluated by:
(a) visual examination of the fluid for the amount of sludge formed, if any;
(b) measuring the percent change in viscosity from the preoxidation level;
(c) measuring the change in the acid number of the oxidized fluid;
(d) measuring the change in weight of the metals after oxidation; and,
(e) measuring the percent loss, if any, in the weight of the oxidized fluid.

The measure of stability of the stabilized fluid is determined by comparison with a control sample of the fluid which is stabilized with 0.75 parts (phr) of p,p'-dioctyl-diphenylamine (commercially available under the trademark Stalite S* from the B. F. Goodrich Company, Akron, Ohio), per 100 parts of synthetic ester functional fluid. In general, the % viscosity change obtained with the compounds of this invention are comparable with, or lower than those obtained with Stalite S* at equivalent concentrations.
*trademark of The B. F. Goodrich Company The ultraviolet light stability of compositions of this invention, for example, synthetic resins used for construction and other industrial applications, is evaluated by exposing samples of the compositions, and blanks, to a Xenon or carbon arc light in a Weather-O-meter operating at temperatures of about 60° C. The sample is considered to have been photodegraded when it has lost in excess of fifty percent (50) of its tensile strength as determined by ASTM D 638-76. In a typical test, a preselected quantity of a stabilizer compound, an antioxidant and other optional processing aids are compounded with a resin such as polypropylene or other polyolefin, and then compression molded into sheets about 20 mils thick from which dumb-bell-shaped test specimens are cut. At 500 hours, or other preselected intervals, a test specimen is removed from the Weather-O-meter and its tensile strength measured on an Instron tensile testing device.

The following Table I sets forth data obtained on tests conducted with 20 mil thickness samples of polypropylene. All samples contain 0.125 parts stabilizer compound per 100 parts resin ('phr') and also include 0.25 phr of Irganox 1010 antioxidant.

TABLE I

| Stabilizer Compound | Xenon Weather-O-meter(hours) |
|---|---|
| Blank with 0.25 phr Irganox 1010 | 180 |
| 2-(4-2,2,6,6-tetramethylpiperidine)-amino-2-methyl-N—(4-2,2,6,6-tetramethylpiperidine)-propionamide (m. pt. 125-7° C.) | 2600 |
| 2-(4-2,2,6,6-tetramethylpiperidine)-amino-2-phenyl-N—(4-2,2,6,6-tetramethylpiperidine)-propionamide (m. pt. 113-5° C.) | 2480 |
| 2-(4-2,2,6,6-tetramethylpiperidine)-amino-2-methyl-N—(4-2,2,6,6-tetramethylpiperidine)-butanamide (m. pt. 110-2° C.) | 2600 |
| 2-(4-2,2,6,6-tetramethylpiperidine)-amino-2-methyl-N—(4-2,2,6,6-tetramethylpiperidine)-octanamide (m. pt. 108-9° C.) | 2600 |
| 2-(4-2,2,6,6-tetramethylpiperidine)-amino-2,2-pentamethylene-N—(4-2,2,6,6-tetramethyl-piperidine)-acetamide (m. pt. 132-5° C.) | 2600 |

*The sample tested contains the specified stabilizer compound prepared in a manner analogous to that described in Example 2 hereinabove.
+available from American Cyanamid Co.

The above-tested compounds are among the most preferred, characterized in that each has an alkyleneimine substituent on at least the amine N atom, and this substituent is preferably substituted at the N-adjacent carbon atoms of the alkyleneimine ring. The reactant used to effect the desired substitution may be a primary or secondary alkyleneimine amine, most preferably with tetraalkyl susbtituents.

I claim:

1. A stabilized composition of matter which comprises a UV light sensitive synthetic resinous material or synthetic lubricant subject to the deleterious effects of oxygen and heat and from about 0.001 percent to about 10 percent weight of a substituted alpha-aminoacetamide of the formula

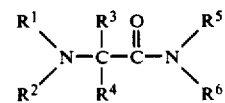

wherein
- at least one of R$^1$, R$^2$, R$^5$ and R$^6$ substituents is alkylene imine having from 5 to 8 carbon atoms in which hydrogen atoms may be substituted with alkyl groups having from 1 to about 24 carbon atoms, and, when one substituent on either N atom is alkylene imine, the other substituent on that N atom represents hydrogen or said alkyl; and
- R$^3$ and R$^4$ independently represent the following substituents: hydrogen; aryl, alkyl having from 1 to about 24 carbon atoms wherein functional groups may be substituted with alkyl groups; hydroxyalkyl having from 1 to about 12 carbon atoms; haloalkyl having from 1 to about 12 carbon atoms; cyanoalkyl having from 2 to about 12 carbon atoms; aminoalkyl or iminoalkyl having from 1 to about 12 carbon atoms; ether groups having from 3 to about 18 carbon atoms; hydroxyalkyl ether or cyanoalkyl ether groups having from 4 to about 18 carbon atoms; alkenyl and aralkyl having from 7 to about 14 carbon atoms; alkylene having from 1 to about 7 carbon atoms; alkenylene having from 2 to about 10 carbon atoms; each substituent optionally containing a phosphite, ester or hindered phenol group, and each substituent in combination, R$^3$ with R$^4$, may form a ring containing from about 5 to about 9 ring atoms, which ring may also contain hetero atoms such as N, S or O, and optionally contain a keto, ester, amide, ether or thio group.

2. The stabilized composition of claim 1 wherein,
R$^1$ is alkyleneimine which is optionally substituted, and R$^2$ is selected from the group consisting of hydrogen and said alkyl;
R$^3$ and R$^4$ are selected from the group consisting of aryl which is optionally substituted, said alkyl, hydroxyalkyl, and, R$^3$ and R$^4$ in combination form alkylene having from 5 to about 7 ring atoms; and,
R$^5$ and R$^6$ are each selected from the group consisting of hydrogen and said alkyl, providing that if one is hydrogen the other is said alkyl.

3. The stabilized composition of claim 1 wherein,
R$^1$ is alkyleneimine which is optionally substituted, and R$^2$ is selected from the group consisting of hydrogen and said alkyl;
R$^3$ and R$^4$ are selected from the group consisting of aryl which is optionally substituted, said alkyl, hydroxyalkyl, and, R$^3$ and R$^4$ in combination form alkylene having from 5 to about 7 ring atoms; and
R$^5$ in combination with R$^6$ form morpholine.

4. The stabilized composition of claim 1 wherein,
R$^1$ is alkyleneimine which is optionally substituted, and R$^2$ is selected from the group consisting of hydrogen and said alkyl;
R$^3$ and R$^4$ are selected from the group consisting of aryl which is optionally substituted, said alkyl, hydroxyalkyl, and, R$^3$ and R$^4$ in combination form alkylene having from 5 to about 7 ring atoms; and,
R$^5$ is alkyleneimine which is optionally substituted, and R$^6$ is selected from the group consisting of hydrogen and said alkyl.

5. A catalytic method for directly preparing a substituted alpha-aminoacetamide having the formula

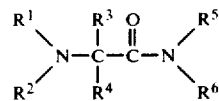

wherein,
- at least one of R$^1$, R$^2$, R$^5$ and R$^6$ substituents is alkyleneimine having from 5 to 8 carbon atoms in which hydrogen atoms may be substituted with alkyl groups having from 1 to about 24 carbon atoms, and, when one substituent on either N atom is alkyleneimine, the other substituent on that N atom represents hydrogen or said alkyl; and,
- R$^3$ and R$^4$ independently represent the following substituents: hydrogen; aryl, alkyl having from 1 to about 24 carbon atoms wherein functional groups may be substituted with alkyl groups; hydroxyalkyl having from 1 to about 12 carbon atoms; haloalkyl having from 1 to about 12 carbon atoms; cyanoalkyl having from 2 to about 12 carbon atoms; aminoalkyl or iminoalkyl having from 1 to about 12 carbon atoms; ether groups having from 3 to about 18 carbon atoms; hydroxyalkyl ether or cyanoalkyl ether groups having from 4 to about 18 carbon atoms; alkenyl and aralkyl having from 7 to about 14 carbon atoms; alkylene having from 1 to about 7 carbon atoms; alkylene having from 2 to about 10 carbon atoms; each substituent optionally containing a phosphite, ester or hindered phenol group, and each substituent in combination, R$^3$ with R$^4$, may form a ring containing from about 5 to about 9 ring atoms, which ring may also contain hetero atoms such as N, S or O, and optionally contain a keto, ester, amide, ether or thio group; comprising, reacting (a) an alkyleneimine amine nucleophilic agent with (b) a carbonyl compound and (c) a trichloromethide generating agent, in an aqueous alkaline medium, at a relatively low temperature in th range from $-20°$ C. to about 50° C., in the presence of a catalytic amount of an onium salt sufficient to yield said substituted alpha-aminoacetamide.

6. The catalytic method of claim 5 wherein said alkyleneimine amine nucleophilic agent is selected from the group consisting of primary and secondary amines, said alkoxide ion generating agent is selected from the group consisting of ketones and aldehydes, and said trichloromethide generating agent is chloroform.

7. The catalytic method of claim 6 wherein said onium salt has the formula

wherein
Y is selected from the group consisting of N, P and S;
R represents either different of identical monovalent organic radicals bonded to Y;
X$^-$ is a counterion selected from the group consisting of Cl, Br, I, F, SO$^=_4$ and HSO$_4^=$; and,
n is an integer which is 3 when Y is S, and which is 4 when Y is N or P.

8. The catalytic method of claim 7 wherein said onium salt has the formula

wherein
Y is N or P, and $R_a$–$R_d$ are monovalent hydrocarbon radicals selected from the group consisting of alkyl, alkenyl, aryl, alkaryl, aralkyl, and cycloalkyl radicals, optionally substituted with suitable heteroatom-containing functional groups.

9. The catalytic method of claim 8 wherein said onium salt is a quaternary onium salt of N or P and the total number of carbon atoms is in the range from about 15 to about 40.

10. A substituted alpha-aminoacetamide compound having the formula

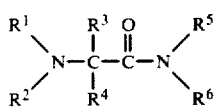

wherein,
at least one of $R^1$, $R^2$, $R^5$ and $R^6$ substituents is alkyleneimine having from 5 to 8 carbon atoms in which hydrogen atoms may be substituted with alkyl groups having from about 1 to about 24 carbon atoms, and, when one substituent on either N atom is alkyleneimine, the other substituent on that N atom represents hydrogen or said alkyl; and, $R^3$ and $R^4$ independently represent the following substituents; hydrogen; aryl, alkyl having from 1 to about 24 carbon atoms wherein functional groups may be substituted with alkyl groups; hydroxyalkyl having from 1 to about 12 carbon atoms; haloalkyl having from 1 to about 12 carbon atoms; cyanoalkyl having from 2 to about 12 carbon atoms; aminoalkyl or iminoalkyl having from 1 to about 12 carbon atoms; ether groups having from 3 to about 18 carbon atoms; hydroxyalkyl ether or cyanoalkyl ether groups having from 4 to about 18 carbon atoms; alkenyl and aralkyl having from 7 to about 14 carbon atoms; alkylene having from 1 to about 7 carbon atoms; alkenylene having from 2 to about 10 carbon atoms; each substituent optionally containing a phosphite, ester or hindered phenol group, and each substituent in combination, $R^3$ with $R^4$, may form a ring containing from about 5 to about 9 ring atoms, which ring may also contain hetero atoms such as N, S or O, and optionally contain a keto, ester, amide, ether or thio group.

11. The of claim 10 wherein,
$R^1$ is alkyleneimine which is optionally substituted, and $R^2$ is selected from the group consisting of hydrogen and said alkyl;
$R^3$ and $R^4$ are selected from the group consisting of aryl which is optionally substituted, said alkyl, hydroxylalkyl, and, $R^3$ and $R^4$ in combination form alkylene having from 5 to about 7 ring atoms; and
$R^5$ and $R^6$ are each selected from the group consisting of hydrogen and said alkyl, providing that if one is hydrogen the other is said alkyl.

12. The compound of claim 10 wherein,
$R^1$ is alkyleneimine which is optionally substituted, and $R^2$ is selected from the group consisting of hydrogen and said alkyl;
$R^3$ and $R^4$ are selected from the group consisting of aryl which is optionally substituted, said alkyl, hydroxyalkyl, and, $R^3$ and $R^4$ in combination form alkylene having from 5 to about 7 ring atoms; and,
$R^5$ in combination with $R^6$ form morpholine.

13. The compound of claim 10 wherein,
$R^1$ is alkyleneimine which is optionally substituted, and $R^2$ is selected from the group consisting of hydrogen and said alkyl;
$R^3$ and $R^4$ are selected from the group consisting of aryl which is optionally substituted, said alkyl, hydroxyalkyl, and, $R^3$ and $R^4$ in combination form alkylene having from 5 to about 7 ring atoms; and,
$R^5$ is alkyleneimine which is optionally substituted, and $R^6$ is selected from the group consisting of hydrogen and said alkyl.

14. An alkyleneimine-substituted 2-aminoacetamide selected from the group consisting of:
2-(4-2,2,6,6-tetramethylpiperidine)-amino-2-pentamethylene-diethylacetamide;
2-(4-2,2,6,6-tetramethylpiperidine)-amino-2-methyl-N-(4-2,2,6,6-tetramethylpiperidine)-butanamide;
2-dimethyl,2-(4-2,2,6,6-tetramethylpiperidine)-aminoacetamorpholinide;
2-(4-2,2,6,6-tetramethylpiperidine)-amino-2-methyl-N-(4-2,2,6,6-tetramethylpiperidine)-propionamide;
2-(4-2,2,6,6-tetramethylpiperidine)-amino-2-phenyl-N-(4-2,2,6,6-tetramethylpiperidine)-butanamide;
2-(4-2,2,6,6-tetramethylpiperidine)-amino-2-methyl-N-(4-2,2,6,6-tetramethylpiperidine)-octanamide; and
2-(4-2,2,6,6-tetramethylpiperidine)-amino-2,2-pentamethylene-N-(4-2,2,6,6-tetramethylenepiperidine)-acetamide.

15. The compound of claim 13 wherein said alkyleneimine substituent has substituents on C atoms adjacent the ring N atom of said alkyleneimine.

16. The compound of claim 15 wherein said substituents are said alkyl.

* * * * *

UNITED STATES PATENT AND TRADEMARK OFFICE
CERTIFICATE OF CORRECTION

PATENT NO. : 4,601,839
DATED : July 22, 1986
INVENTOR(S) : John T. Lai

It is certified that error appears in the above—identified patent and that said Letters Patent is hereby corrected as shown below:

Column 16, line 40; "in th range from -20°C to about 50°C"; should read -- in th range from about -20°C to about 50°C --

Column 17, line 25; "having from about 1 to about 24 carbon atoms"; should read -- having from 1 to about 24 carbon atoms --

Column 18, line 46; "tetramethylenepiperidine"; should read -- tetramethylpiperidine --

Signed and Sealed this

Fifth Day of July, 1988

Attest:

DONALD J. QUIGG

Attesting Officer

Commissioner of Patents and Trademarks